United States Patent
Liu et al.

(10) Patent No.: US 11,013,553 B2
(45) Date of Patent: May 25, 2021

(54) TREATMENT METHOD FOR HYPERTROPHIC CARDIOMYOPATHY

(71) Applicant: Hangzhou Nuo Cheng Medical Instrument Co., Ltd, Hangzhou (CN)

(72) Inventors: Liwen Liu, Hangzhou (CN); Tingchao Zhang, Hangzhou (CN); Yang Li, Hangzhou (CN); Bobo Peng, Hangzhou (CN); Xinjiong Qiu, Hangzhou (CN)

(73) Assignee: HANGZHOU NUO CHENG MEDICAL INSTRUMENT CO., LTD., Hangzhou (CN)

( * ) Notice: Subject to any disclaimer, the term of this patent is extended or adjusted under 35 U.S.C. 154(b) by 442 days.

(21) Appl. No.: 16/202,248

(22) Filed: Nov. 28, 2018

(65) Prior Publication Data

US 2019/0159832 A1    May 30, 2019

(30) Foreign Application Priority Data

Nov. 28, 2017  (CN) .......................... 201711213683.9
Aug. 24, 2018  (CN) .......................... 201810971599.1

(51) Int. Cl.
*A61B 18/14*   (2006.01)
*A61B 18/18*   (2006.01)
(Continued)

(52) U.S. Cl.
CPC ...... *A61B 18/1477* (2013.01); *A61B 10/0233* (2013.01); *A61B 18/1815* (2013.01);
(Continued)

(58) Field of Classification Search
CPC ............ A61B 18/1477; A61B 18/1815; A61B 2018/00023; A61B 2018/00202;
(Continued)

(56) References Cited

U.S. PATENT DOCUMENTS 6,117,152 A   9/2000  Huitema
6,770,070 B1  8/2004  Balbierz
(Continued)

FOREIGN PATENT DOCUMENTS

CN   101410062 A   4/2009
CN   101579256 A   11/2009
(Continued)

OTHER PUBLICATIONS

International Search Report issued in International Application No. PCT/CN2019/090923, dated Aug. 13, 2019, China National Intellectual Property Administration, Beijing.
(Continued)

*Primary Examiner* — Michael F Peffley
(74) *Attorney, Agent, or Firm* — Hauptman Ham, LLP

(57) ABSTRACT

The present disclosure provides a treatment method for hypertrophic cardiomyopathy applied to an ablation system comprising an ablation needle assembly and an energy generating device coupled to the ablation needle assembly. The treatment method comprises: advancing a distal end of the ablation needle assembly from an outside of a body through an intercostal and a cardiac apex into a ventricular septum; turning on the energy generating device, and using the distal end of the ablation needle assembly to perform radio-frequency ablation or microwave ablation to hypertrophied myocardium within the ventricular septum to make it necrotic and/or atrophic. The present disclosure avoids risk and pain of surgical septal myectomy and extracorporeal circulation in surgical resection, and does not have risk of large-area myocardial infarction caused by alcohol ablation. It is easy to operate and slight trauma to patients.

19 Claims, 8 Drawing Sheets

(51) Int. Cl.
*A61B 10/02* (2006.01)
*A61B 18/00* (2006.01)
*A61B 90/00* (2016.01)

(52) U.S. Cl.
CPC .............. *A61B 2018/00023* (2013.01); *A61B 2018/00202* (2013.01); *A61B 2018/00357* (2013.01); *A61B 2018/00577* (2013.01); *A61B 2018/00666* (2013.01); *A61B 2018/00702* (2013.01); *A61B 2018/00714* (2013.01); *A61B 2018/00738* (2013.01); *A61B 2018/00791* (2013.01); *A61B 2018/00982* (2013.01); *A61B 2018/1425* (2013.01); *A61B 2018/1475* (2013.01); *A61B 2018/1869* (2013.01); *A61B 2018/1892* (2013.01); *A61B 2090/061* (2016.02); *A61B 2090/378* (2016.02)

(58) Field of Classification Search
CPC ........... A61B 2018/00357; A61B 2018/00577; A61B 2018/00666; A61B 2018/00702; A61B 2018/00714; A61B 2018/0738; A61B 2018/00791; A61B 2018/00982; A61B 2018/1425; A61B 2018/1869; A61B 2018/1892; A61B 2090/061; A61B 2090/378
See application file for complete search history.

(56) References Cited

U.S. PATENT DOCUMENTS

| | | | | |
|---|---|---|---|---|
| 6,802,319 | B2* | 10/2004 | Stevens | A61B 17/00234 128/898 |
| 7,749,157 | B2* | 7/2010 | Bertolero | A61B 5/24 600/116 |
| 2008/0045890 | A1* | 2/2008 | Seward | A61M 25/1002 604/93.01 |
| 2009/0069808 | A1* | 3/2009 | Pike, Jr. | A61B 18/1492 606/49 |
| 2011/0125144 | A1* | 5/2011 | Edgerton | A61B 18/1402 606/33 |
| 2014/0121658 | A1 | 5/2014 | Cosman, Jr. et al. | |
| 2015/0126922 | A1 | 5/2015 | Willis | |
| 2016/0135872 | A1 | 5/2016 | Minnelli et al. | |

FOREIGN PATENT DOCUMENTS

| | | | |
|---|---|---|---|
| CN | 102933167 | A | 2/2013 |
| CN | 104688333 | A | 6/2015 |
| CN | 105578981 | A | 5/2016 |
| CN | 105943159 | A | 9/2016 |
| CN | 106618727 | A | 5/2017 |
| CN | 106806019 | A | 6/2017 |
| CN | 206390989 | U | 8/2017 |
| CN | 107949336 | A | 4/2018 |
| CN | 207253372 | U | 4/2018 |
| CN | 208435787 | U | 1/2019 |
| CN | 109350233 | A | 2/2019 |
| CN | 109350234 | A | 2/2019 |
| CN | 109833089 | A | 6/2019 |
| CN | 109833091 | A | 6/2019 |
| WO | 9944506 | A1 | 9/1999 |
| WO | 03061499 | A1 | 7/2003 |

OTHER PUBLICATIONS

International Search Report issued in International Application No. PCT/CN2019/099087, dated Oct. 29, 2019, China National Intellectual Property Administration, Beijing.
International Search Report issued in International Application No. PCT/CN2019/106745, dated Dec. 12, 2019, China National Intellectual Property Administration, Beijing.
International Search Report issued in International Application No. PCT/CN2019/106747, dated Dec. 12, 2019, China National Intellectual Property Administration, Beijing.

* cited by examiner

A-A

TREATMENT METHOD FOR HYPERTROPHIC CARDIOMYOPATHY

TECHNICAL FIELD

This present disclosure relates to medical fields, and in particular relates to a treatment method for hypertrophic cardiomyopathy.

BACKGROUND

Hypertrophic cardiomyopathy (Hereinafter "HCM") is a common autosomal dominant cardiovascular disease with an incidence of about 1:500 in the general population and a mortality rate of 1.4%-2.2%. HCM has a large difference in natural medical history. Some patients have no obvious clinical symptoms, but HCM can also cause chest tightness, chest pain, difficulty breathing, repeated syncope, atrial fibrillation, ventricular tachycardia, heart failure, etc., which are the most common causes of sudden death in youngsters and athletes.

The main manifestation of HCM is left ventricular (hereinafter "LV") having one or more segmental hypertrophy, and the general diagnostic criteria is thickness greater than or equal to 15 mm. When the systolic anterior motion (hereinafter "SAM") appears against the ventricular septum, causing stenosis or even obstruction of the left ventricular outflow tract (hereinafter "LVOT"), that is, when the pressure difference of the LVOT is too large, which is called as hypertrophic obstructive cardiomyopathy (Hereinafter "HOCM"). HOCM accounts for about 70% of HCM patients. At present, the treatment strategy for HCM is to expand LVOT to reduce the pressure difference and reduce its obstruction. The treatment methods mainly include drug treatment, surgical septal myectomy and alcohol septal ablation.

The drug treatment is relatively simple and easy, and patients have no pain in surgery, but some patients have poor drug efficacy or intolerance. The surgical septal myectomy, that is, modified morrow surgery is to remove the hypertrophic myocardium by surgical thoracotomy. The main resection position is an anterior of the ventricular septum and concentrated in a surface of the left ventricular. The thickness of the ventricular septum after resection can be reduced by 50%, the postoperative LVOT is significantly reduced, but there is a certain risk of modified morrow surgery, and the patient's postoperative recovery is more painful. The alcohol septal ablation is an interventional treatment method, which mainly uses percutaneous transluminal coronary angioplasty to deliver a balloon into a septal branch to be eliminated, and slowly inject alcohol into the septal branch to cause chemical occlusion, which can reduce myocardial ischemia, necrosis, thinning, and reduce LVOT in hypertrophic ventricular septum. Although this method avoids the pain of surgery, in clinical application, alcohol may cause myocardial infarction through the branch vessel, and there is still a certain risk.

SUMMARY

The present disclosure provides a treatment method for hypertrophic cardiomyopathy with less tissue damage and significant curative effect.

The present disclosure provides a treatment method for hypertrophic cardiomyopathy, applied to an ablation system. The ablation system comprises an ablation needle assembly and an energy generating device coupled to the ablation needle assembly. The treatment method for hypertrophic cardiomyopathy comprises: advancing a distal end of the ablation needle assembly from an outside of a body through an intercostal and a cardiac apex into a ventricular septum; turning on the energy generating device, and using the distal end of the ablation needle assembly to perform radio-frequency ablation or microwave ablation to hypertrophied myocardium within the ventricular septum, destroying activity of the hypertrophied myocardium within the ventricular septum, and making the hypertrophied myocardium within the ventricular septum necrotic and/or atrophic.

Compared with a prior art, the treatment method for hypertrophic cardiomyopathy of the present disclosure has at least the following beneficial effects:

In the present disclosure, the distal end of the ablation needle assembly is advanced into the ventricular septum through the intercostal and the cardiac apex, and the hypertrophied myocardium within the ventricular septum is subjected to radio-frequency ablation or microwave ablation, which destroys activity of the hypertrophied myocardium within the ventricular septum, and causes necrosis and/or atrophy of the hypertrophied myocardium at the ablation position to thin the hypertrophied myocardium, thereby widening outflow tract of the left ventricular, removing obstruction, and preventing the ventricular septum from further thicken to a great extent, improving the function and the hemodynamics of the heart, which is not only avoiding the risk and pain of surgical septal myectomy and extracorporeal circulation in surgical resection, but also having no risk of large-area myocardial infarction caused by alcohol ablation or alcohol spillover. It is easy to operate and slight trauma to patients. The risk of the treatment method for hypertrophic cardiomyopathy is low and the curative effect is remarkable.

BRIEF DESCRIPTION OF THE ACCOMPANYING DRAWINGS

To better illustrate the embodiments of the present disclosure, a brief description of the accompanying drawings for use with the illustration of the embodiments is provided below. It is evident that the drawings described below depict merely some embodiments and those of ordinary skill in the art can obtain other drawings based on the arrangements shown in these drawings without making inventive efforts.

DETAILED DESCRIPTION OF ILLUSTRATED EMBODIMENTS

The technical solution in the embodiments of the present disclosure will be described clearly and completely hereinafter with reference to the accompanying drawings in the embodiments of the present disclosure. Obviously, the described embodiments are merely some but not all the embodiments of the present disclosure. All other embodiments obtained by a person of ordinary skilled in the art based on the embodiments of the present disclosure without creative efforts shall all fall within the protection scope of the present disclosure.

In order to describe the structure of the ablation needle assembly and the ablation system more clearly, the terms "proximal/proximal end" and "distal/distal end" are defined herein as a common term in the field of interventional medicine. Specifically, the "proximal/proximal end" is referred to an end close to an operator during a surgical procedure, and the "distal/distal end" is referred to an end away from the operator during the surgical procedure.

Unless otherwise defined, all technical and scientific terms used herein have same meaning with a meaning that is generally understood by those skilled in the art. The term used in the specification of the present disclosure is for purpose of describing particular embodiments and is not intended to be limiting.

Figure 1:
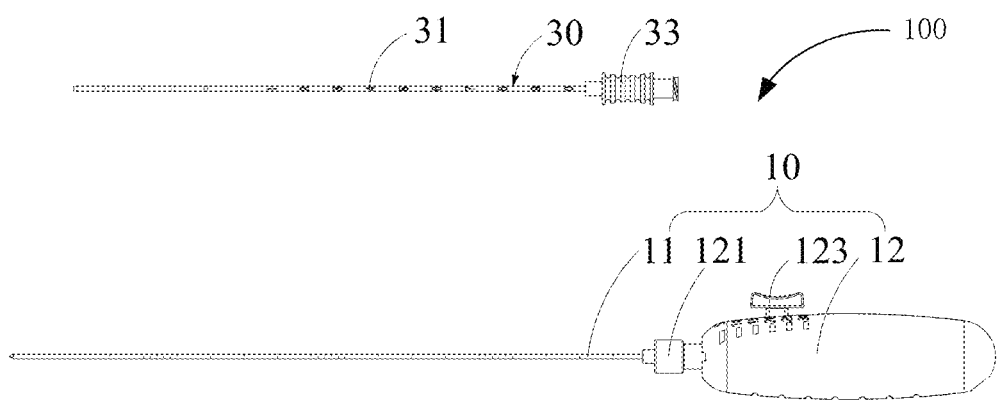
FIG. 1 is a structural schematic diagram of an ablation needle assembly according to one embodiment of the present disclosure.
Figure 2:
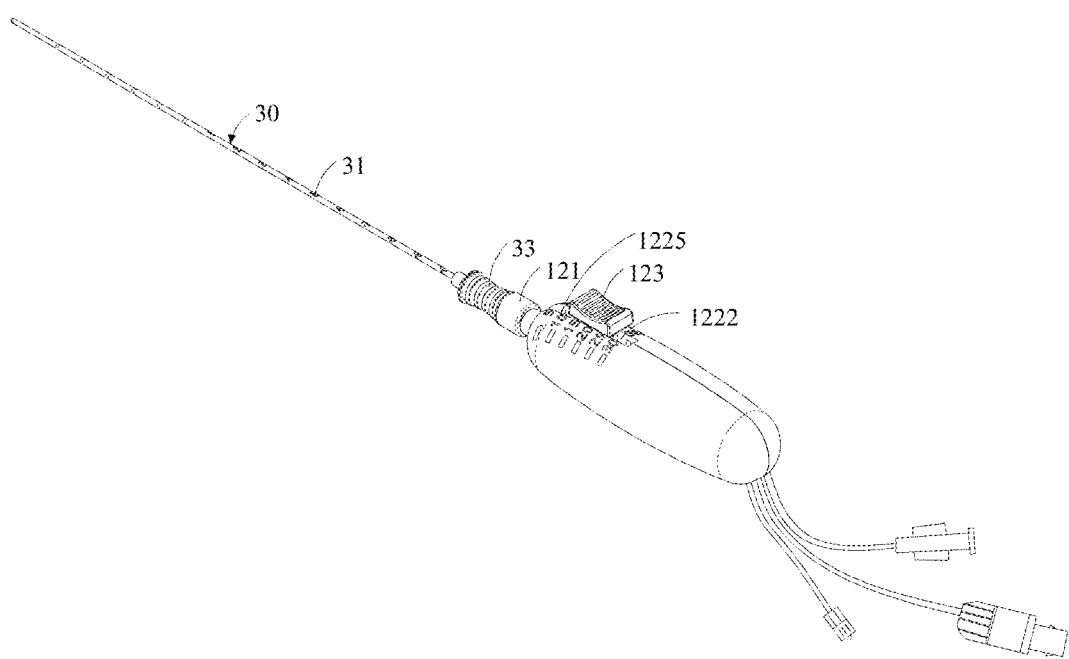
FIG. 2 is a structural schematic diagram of an ablation needle and an outer sleeve assembled according to one embodiment of the present disclosure.
Figure 3:
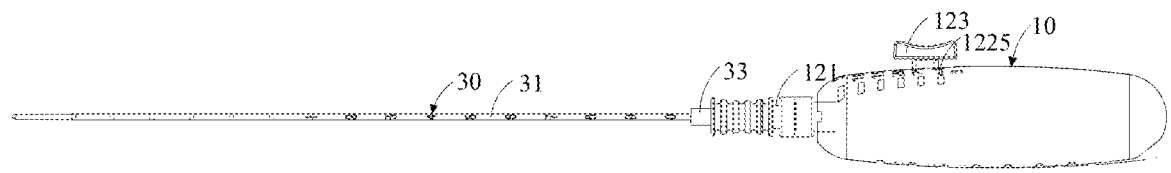
FIG. 3 is a front view of the ablation needle and the outer sleeve assembled as shown in FIG. 2.

As illustrated in FIGS. 1 to 3, the present disclosure provides an ablation needle assembly 100. The ablation needle assembly 100 is used for ablation operation. The ablation needle assembly 100 can include an outer sleeve 30 and an ablation needle 10 that is movably accommodated in the outer sleeve 30. The ablation needle 10 can include an electrode needle body 11 and an ablation handle 12 coupled to a proximal end of the electrode needle body 11. The outer sleeve 30 is sleeved outside the electrode needle body 11 and detachably and rotatably coupled to the ablation handle 12. In the present disclosure, the outer sleeve 30 is at least partially insulated. In other words, the outer sleeve 30 can be completely insulated or partially insulated. A distal end of the electrode needle body 11 can protrude from the outer sleeve 30. When the outer sleeve 30 is completely insulated, a part of the electrode needle body 11 protruding from the outer sleeve 30 is used for performing ablation. When the outer sleeve 30 is partially insulated, the part of the electrode needle body 11 protruding from the outer sleeve 30 and a part of the outer sleeve 30 which is non-insulated are used for performing ablation. Specifically, when the electrode needle body 11 is electrically coupled to a radio-frequency generator, the electrode needle body 11 transmits high-frequency current to cause high-speed oscillation of the charged positive and negative ions in the diseased tissue around the distal end of the electrode needle body 11, and the high-speed oscillation ions generate a large amount of heat due to friction, which causes the temperature in the diseased tissue to rise, causing denaturation of proteins in the diseased cells, loss of water inside and outside the cells, coagulative necrosis of the diseased tissue, and finally formation of myocardial thinning and fibrosis, reducing LVOT, thereby achieving radio-frequency ablation. When the electrode needle body 11 is electrically coupled to a microwave generator, the distal end of the electrode needle body 11 forms a microwave field, and the dipole molecules such as water molecules in the diseased tissue generate heat under the action of the microwave field due to the movement friction and the violent collision, so that the temperature in the diseased tissue rises, the protein in the diseased cells is denatured, the water inside and outside the cells is lost, the coagulation necrosis occurs in the diseased tissue, and finally the myocardial is thinned and the fibrosis is formed, and the LVOT is reduced, thereby achieving microwave ablation. In addition, the outer sleeve 30 is detachably coupled to the ablation handle 12. Therefore, after completing ablation operation, the ablation needle 10 and the outer sleeve 30 can be disassembled, leaving the outer sleeve 30 still in the tissue, providing a channel for other operations, avoiding repeated punctures, reducing tissue damage, and capable of making the ablation and other operations more convenient and efficient. Furthermore, the ablation handle 12 can be rotatable relatively to the outer sleeve 30, which causes the electrode needle body 11 to rotate relatively to the outer sleeve 30. That is, the outer sleeve 30 and the electrode needle body 11 of the ablation needle 10 are not integrated, when it is necessary to rotate the ablation needle 10, the outer sleeve 30 can be maintained still, thereby reducing tissue damage, and the resistance of rotation is less.

Figure 4:
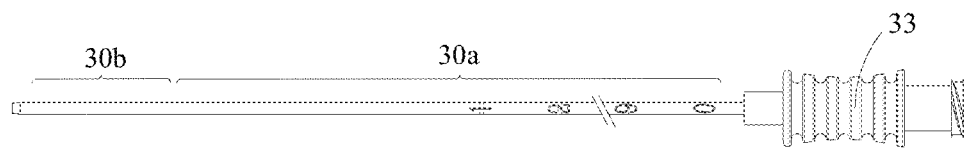
FIG. 4 is a structural schematic diagram of the outer sleeve according to one embodiment of the present disclosure.

The outer sleeve 30 is at least partially insulated. Preferably, the outer sleeve 30 is completely insulated. As shown in FIG. 4, the outer sleeve 30 is at least partially insulated, refers that, the first sleeve portion 30a of the outer sleeve 30 close to the proximal end is insulated, and the second sleeve portion 30b of the outer sleeve 30 close to the distal end may be non-insulated, such that the non-insulated portion of the outer sleeve 30 can also transmit high frequency current or microwaves to increase an ablation region. The outer sleeve 30 may be at least partially made of insulating materials, or the outer sleeve 30 may be entirely made of non-insulating materials and then at least partially coated with an insulating coating on an outer surface of the outer sleeve 30. When performing the ablation operation, the portion of the outer sleeve 30 coated with the insulating layer serves as an insulating sleeve of the ablation needle 10. In order to improve the supportability of the outer sleeve 30, and to facilitate the puncture of human tissue, preferably, the outer sleeve 30 is made of metal materials, and the outer surface of the outer sleeve 30 is coated with an insulating coating. The metal material can include but is not limited to 304 stainless steel, 321 stainless steel or 631 stainless steel. The insulating coating can include but is not limited to PTFE coating, titanium nitride coating, parylene coating and the like. The metal material for making the outer sleeve 30 should have sufficient hardness to puncture human tissue, and at the same time, it needs to have excellent biocompatibility, and small coefficient of friction. The insulating coating should have reliable insulativity, excellent biocompatibility, and small coefficient of friction. At the same time, the insulating coating requires an intimate bond to the outer surface of the outer sleeve 30, the insulating coating is not easy to fall off, for example, 304 stainless steel tube with PTFE coating, 304 stainless steel tube with parylene coating, 321 stainless steel tube with titanium nitride coating, or 631 stainless steel tube with parylene coating, or the like. Considering the insulation reliability and process feasibility, the thickness of various insulating coatings should be equal or greater than 3 μm. It can be understood that, in other embodiments, the outer sleeve 30 can also be completely made of insulating materials, such as a plastic tube made of PEEK, PI or PA materials, which can meet the hardness requirement, or a ceramic tube made of alumina porcelain, talc porcelain or boron nitride materials, or the like.

The distal end of the outer sleeve 30 can have an either straight or beveled tip. Preferably, the distal end of the outer sleeve 30 is a beveled tip so that the respective positions of the outer sleeve 30 can be inserted into the tissue easily, and the contact area of the tissue around the outer sleeve 30 with the electrode needle body 11 is different, thereby the desired ablation region is determined according to anatomical structure of the tissue to be treated, the orientation and localization ablation are achieved by adjusting the inserting direction of the outer sleeve 30.

In one embodiment, one or more hollow region (not shown) are defined axially or circumferentially on a side wall of the distal end of the outer sleeve 30. When the outer sleeve 30 rotates or moves relatively to the electrode needle body 11, the overlapping position between the hollow region and the energy release region on the electrode needle body 11 is changed. Therein, the energy release region refers to a region where the electrode needle body 11 can radiate energy. By changing the overlapping position of the hollow region and the energy release region, the exposed area of the energy release region can be adjusted continuously or gradiently, and the ablation region and the ablation orientation can be adjusted. The change rate of the exposed area of the energy release region can also be controlled by changing the shape of the inner edge of the hollow region, that is, the amount of change of the exposed area can be adjusted under the same stroke of the outer sleeve 30.

Furthermore, the hollow regions are coupled in one piece, or are multiple arranged at intervals.

Furthermore, whether it is for the same energy release region or a plurality of energy release regions, the hollow region may be coupled in one piece or may be arranged at intervals.

For example, it can be realized by rotating the electrode needle body 11 and the outer sleeve 30 relatively to each other. The outer sleeve 30 adopts a hollow structure or a structure that an edge of the distal end is not a regular circle. The energy release region of the electrode needle body 11 may correspond to different hollow region or be blocked by the sidewall of the outer sleeve 30 in the circumferential direction, and the exposed area and/or the position of the energy release region is adjustable, so that the orientation and localization ablation can be realized.

Furthermore, the outer sleeve 30 has a scale identification 31 to indicate a depth of the outer sleeve 30 inserted into the tissue. The scale identification 31 includes a series of scale values, and the scale value gradually increases from the distal end to the proximal end. When the outer sleeve 30 is inserted into the tissue, the depth of the outer sleeve 30 inserted into the tissue can be known by observing the scale value on the outer sleeve 30 corresponding to the body surface of the patient, thereby knowing an approximate position of the outer sleeve 30 inserted into the tissue.

Figure 5:
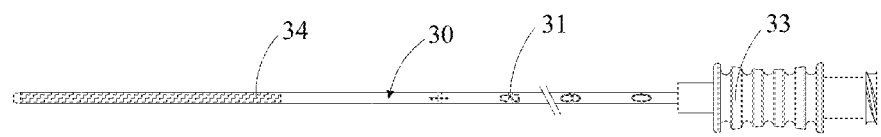
FIG. 5 is a structural schematic diagram of the outer sleeve according to one embodiment of the present disclosure.

Furthermore, as shown in FIG. 5, the distal end of the outer sleeve 30 has a first guiding portion 34 that can be detected by a medical imaging device. The length of the first guiding portion 34 needs to be equal or greater than 5 mm to ensure the accuracy of the position guiding. The first guiding portion 34 can assist the operator in determining whether the distal end of the outer sleeve 30 is advanced along a predetermined puncture path and whether it is approached a predetermined ablation position. Specifically, the first guiding portion 34 may be a structure added at the distal end of the outer sleeve 30, or may be a structure that the distal end of the outer sleeve 30 is processed. Since the ultrasonography is less harmful to the human body than other visualization modes, and is also economical, it is preferable to treat an outer surface of the outer sleeve 30 near the distal end into a rough surface to form the first guiding portion 34 for meet the ultrasonography demand. For example, the surface of the second sleeve portion 30b near the distal end of the outer sleeve 30 may be subjected to a surface roughening treatment such as sandblasting or perforation to form the first guiding portion 34. Moreover, in the present disclosure, the surface roughness of the first guiding portion 34 should not be too high, so that the need for ultrasonography is not affected, and the advancing of the outer sleeve 30 in the tissue is not affected.

The electrode needle body 11 of the ablation needle 10 can be made of biocompatible metal materials having excellent electrical conductivity such as stainless steel. Since the outer sleeve 30 is at least partially insulated, the surface of the electrode needle body 11 of the ablation needle 10 does not need to be coated with insulating materials, which simplifies the manufacturing process of the electrode needle body 11 of the ablation needle 10, and the outer sleeve 30 can support and protect the electrode needle body 11 of the ablation needle 10, thereby allowing the diameter of the electrode needle body 11 to be reduced, for example, the diameter of the electrode needle body 11 can be selected from 20G to 16G, on the one hand to further reduce tissue damage, and on the other hand due to the structure of the tissue of ventricular septum to be ablated is flattening, the smaller the diameter of the electrode needle body 11, the more suitable for ablation of the flat ventricular septum tissue. Furthermore, the problems such as pneumothorax and pericardial effusion during ablation can be prevented, and bleeding can also be reduced. Thus, the ablation needle assembly of the present disclosure is particularly suitable for the ablation treatment of HCM.

The electrode needle body 11 of the ablation needle 10 is electrically coupled to the energy generating device. Therein, the energy generating device may be a microwave generator or a radio-frequency generator. In the case where the outer sleeve 30 is completely insulated, the portion of the electrode needle body 11 of the ablation needle 10 exposed by the outer sleeve 30 transmits microwave energy or radio-frequency energy to the tissue for ablation operation. Preferably, the distal end of the electrode needle body 11 of the ablation needle 10 has a sharp triangular pyramid shape or needle shape, which is advantageous for the combination of the electrode needle body 11 of the ablation needle 10 and the outer sleeve 30 to puncture, and the distal end of the electrode needle body 11 of the ablation needle 10 can also be set to other shapes, such as a sphere, an umbrella, and the like.

Furthermore, referring to FIG. 1 to FIG. 3 and FIG. 6 to FIG. 7, the part of the electrode needle body 11 of the ablation needle 10 contacting the tissue transmits radio-frequency energy or microwave energy to cause high temperature of the tissue, which causes the tissue coagulative necrosis so as to achieve therapeutic purposes. However, if the local temperature is too high, it will affect the normal tissue that does not need to perform ablation operation, and also affect normal monitoring of sensing elements or the medical imaging device. Therefore, the electrode needle body 11 of the ablation needle 10 also defines a cooling channel 16. In this embodiment, the cooling channel 16 is defined in the electrode needle body 11. It can be understood that, in other embodiments, the cooling channel 16 may be defined outside the electrode needle body 11 or partially defined inside the electrode needle body 11 and partially defined outside the electrode needle body 11. The cooling channel 16 is used to deliver a gaseous or liquid cooling medium (such as cooling water) to cool the high temperature portion to control the temperature during the ablation operation. In one embodiment, the cooling channel 16 has a circulating closed channel, and the cooling medium flows in the circulating closed channel in a working state. In another embodiment, the cooling channel 16 is an opening channel, and the distal end of the electrode needle body 11 defines a cooling medium outlet. Specifically, the cooling channel 16 can be selected from the circulating closed channel and the opening channel depending on the type of the cooling medium. Optionally, the circulating closed channel defines a branch outlet at the distal end of the electrode needle body 11, and correspondingly configured with a control valve. A closed or open channel can be achieved through the control valve, the use is more flexible. The control valve can be a solenoid valve or a moving part that can close or open an outlet of the cooling medium. Preferably, the outlet of the cooling medium is located on the end and/or the peripheral wall of the electrode needle body 11. The cooling channel 16 is coupled to a cold source supply device through an extension pipe at the proximal end of the electrode needle body 11. The outlet of the cooling medium can be set at the corresponding position according to the requirements of the output orientation. The control valve can be set at the outlet of the cooling medium to realize the opening and closing of the outlets of the respective cooling medium by switching, shielding and the like.

Figure 24:
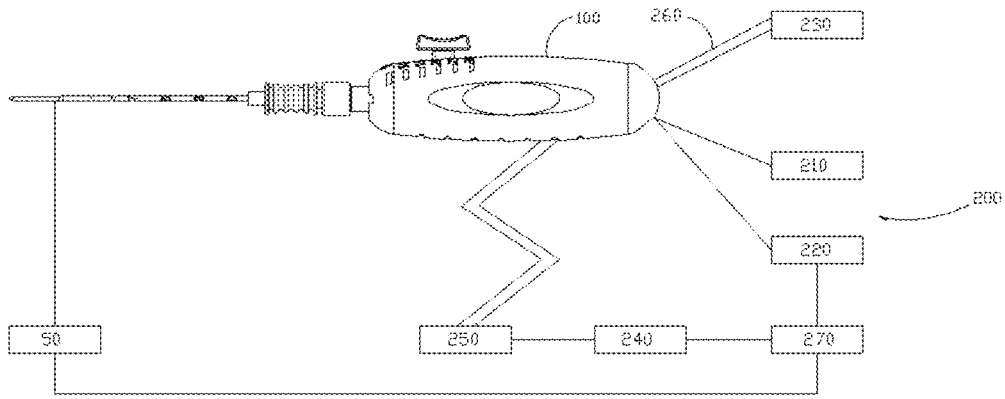
FIG. 24 is a structural schematic diagram showing an ablation system according to one embodiment of the present disclosure.
Figure 25:
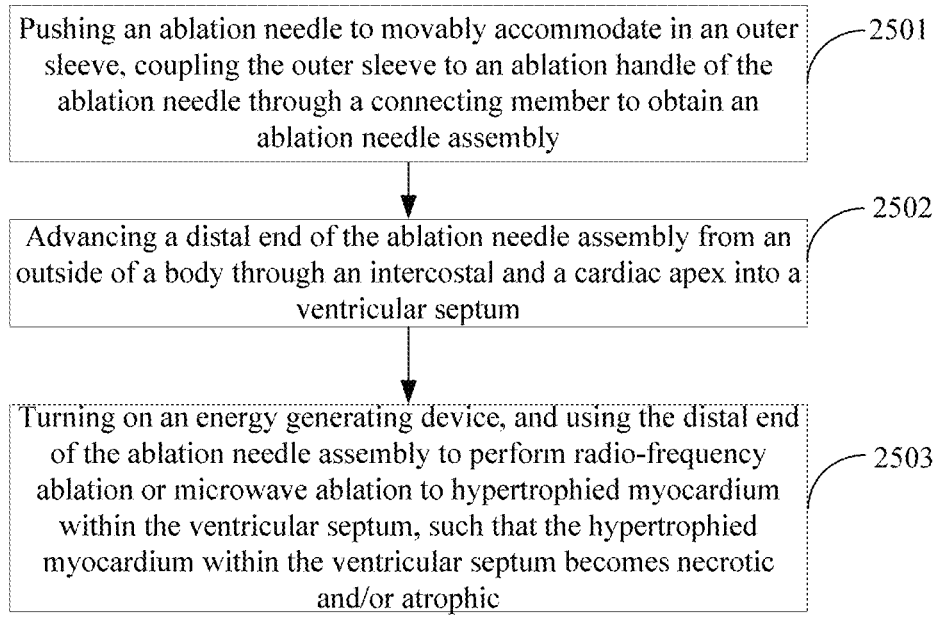
FIG. 25 is a schematic view showing a flowchart of a treatment method for hypertrophic cardiomyopathy according to one embodiment of the present disclosure.

To further enhance temperature monitoring during ablation, the distal end of the ablation needle assembly 100 is provided with a temperature sensor 50 (as shown in FIG. 24). The temperature sensor 50 may be disposed on an inner wall of the distal end of the outer sleeve 30, or attached to an outer wall of the distal end of the electrode needle body 11, or may be disposed in a surface indentation defined at the distal end of the electrode needle body 11 to accommodate the temperature sensor 50, or disposed in a cavity defined on the distal end of the electrode needle body 11.

It can be understood that, in at least one embodiment, the ablation system 100 can further include a data processing device electrically coupled to the temperature sensor 50. As far as the data processing device itself is concerned, it can be a computer, a single chip microcomputer or the like in the prior art to receive, process or display signals sensed by sensing elements. The temperature sensor 50 is electrically coupled to the data processing device by wire or wirelessly. The data processing device adjusts the output parameters of the energy generating device, such as power, etc., based on the results monitored by the temperature sensor 50.

It can be understood that the data processing device can also be integrated with an intraoperative medical imaging device or a simulated navigation device. It can be understood that the data processing device, the medical imaging device or the simulated navigation device can be integrated or separately set in hardware.

Figure 8:
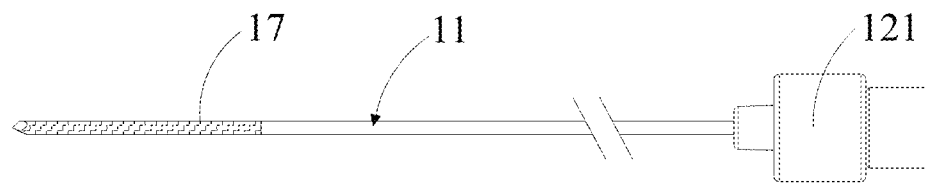
FIG. 8 is a structural schematic diagram of electrode needle body according to one embodiment of the present disclosure.

Furthermore, as shown in FIG. 8, the distal end of the electrode needle body 11 has a second guiding portion 17 that can be detected by the medical imaging device. The length of the second guiding portion 17 needs to be greater or equal to 5 mm. The second guiding portion 17 can assist the operator in determining whether the distal end of the electrode needle body 11 has reached or is in a predetermined ablation position. Specifically, the second guiding portion 17 may be a structure added at the distal end of the electrode needle body 11, or may be obtained by performing a certain treatment on the distal end of the electrode needle body 11. Preferably, the surface of the distal end of the electrode needle body 11 is treated into a rough surface to form the second guiding portion 17 to meet the ultrasonography demand, for example, sandblasting or perforating may be performed on the surface of the distal end of the electrode needle body 11. Moreover, in the present disclosure, the surface roughness of the second guiding portion 17 should not be too high, so that it can meet the need for ultrasonography, and the advancing of the electrode needle body 11 in the tissue is not affected. Therefore, the ablation needle assembly 100 of the present disclosure is particularly suitable for ablation treatment under ultrasonography guidance, and the operator can introduce the distal end of the ablation needle assembly 100 into the ventricular septum of the patient under the ultrasonography guidance. The portion of the electrode needle body 11 exposed by the outer sleeve 30 is to ablate the hypertrophic myocardium.

Figure 9:
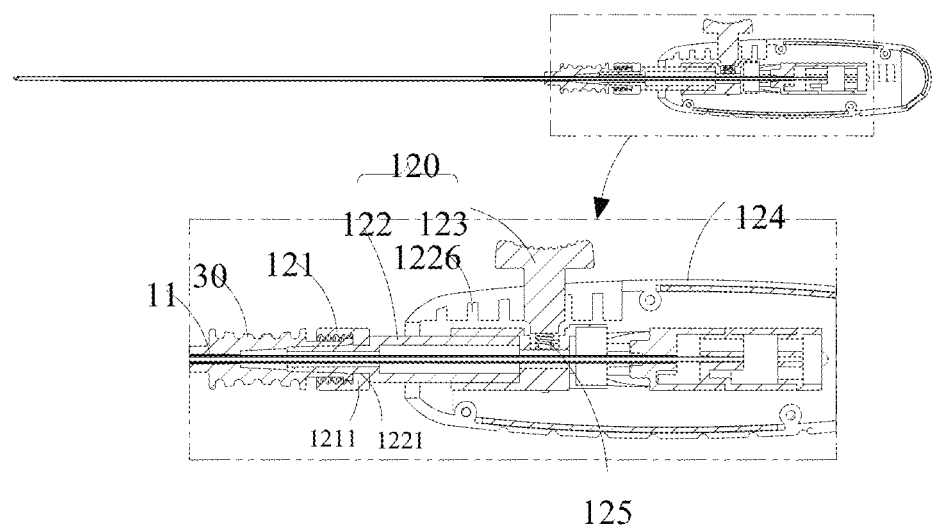
FIG. 9 is a cross-sectional view of the ablation needle and the outer sleeve as shown in FIG. 2.
Figure 11:
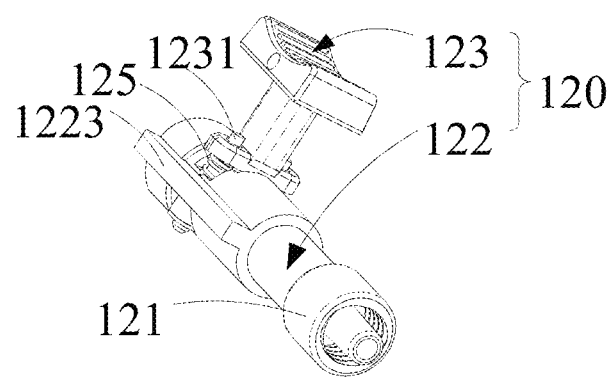
FIG. 11 is a structural schematic diagram of a driving assembly of the ablation needle according to one embodiment of the present disclosure.
Figure 12:
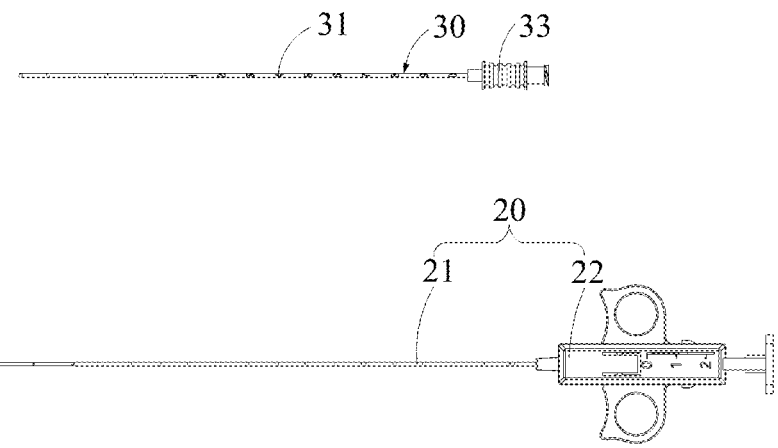
FIG. 12 is an exploded view of a biopsy needle and the outer sleeve according to one embodiment of the present disclosure.
Figure 13:
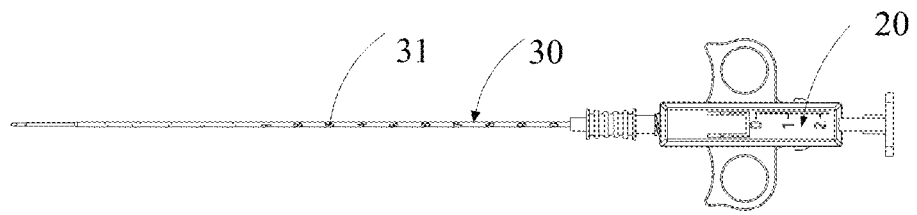
FIG. 13 is a schematic diagram of the biopsy needle and the outer sleeve assembled as shown in FIG. 12.
Figure 14:
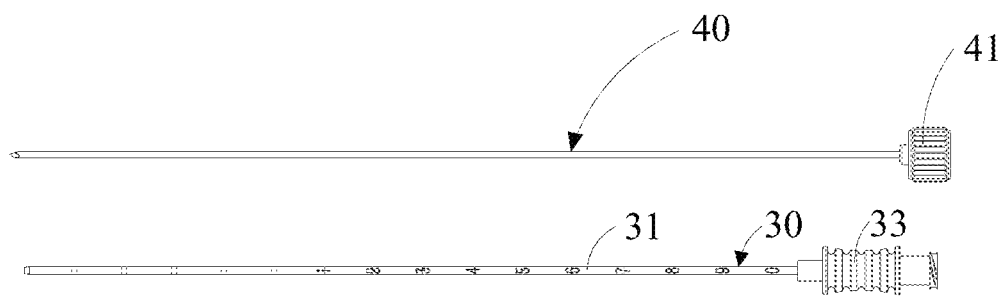
FIG. 14 is an exploded view of a puncture needle and the outer sleeve according to one embodiment of the present disclosure.
Figure 15:
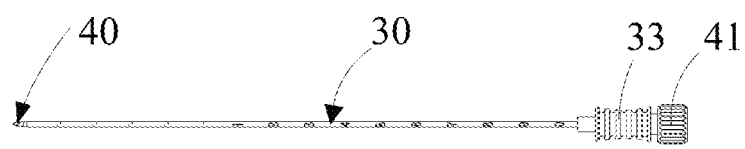
FIG. 15 is a schematic diagram of the puncture needle and the outer sleeve assembled as shown in FIG. 14.
Figure 16:
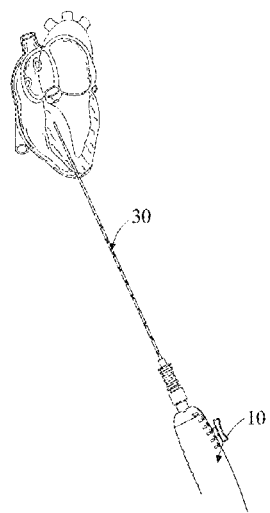
FIG. 16 to FIG. 18 are schematic diagrams showing a use process of the ablation needle assembly according to one embodiment of the present disclosure.

Referring to FIG. 2. FIG. 9, and FIG. 11, the ablation handle 12 can include a driving assembly 120 coupled to the outer sleeve 30 and a connecting member 121 rotatably coupled to the driving assembly 120. The proximal end of the outer sleeve 30 is detachably coupled to the connecting member 121. In other words, the outer sleeve 30 is coupled to the driving assembly 120 through the connecting member 121, and the outer sleeve 30 is driven to move relatively to the electrode needle body 11 along the extending direction of the electrode needle body 11 by the driving assembly 120, so as to adjust the length of the distal end of the electrode needle body 11 protruding from the outer sleeve 30 according to the actual requirement of the ablation range. In this embodiment, the proximal end of the outer sleeve 30 is provided with an external thread, and the distal end of the connecting member 121 is provided with an internal thread for engaging with the external thread of the outer sleeve 30, through the external thread engaged with the internal thread, a detachable connection of the outer sleeve 30 with the connector 121 is thus achieved. Furthermore, in some embodiments of the present disclosure, the outer sleeve 30 is provided with a grip portion 33 located at a position of the external thread towards a side of the distal end of the outer sleeve 30 so as to be rotated relatively to the ablation needle 10 or disassembled from the ablation needle 10. In this embodiment, a plurality of protrusions are provided on the outer wall of the outer sleeve 30 to form the grip portion 33.

Referring to FIG. 9, the driving assembly 120 can include a sliding member 122 disposed axially and an adjusting member 123 coupled to the sliding member 122. The connecting member 121 is coaxially disposed and rotatably coupled to the sliding member 122, that is, the connecting member 121 can be capable of rotating about the axis of the sliding member 122, so that the outer sleeve 30 coupled to the connecting member 121 can be rotated relatively to the sliding member 122. The electrode needle body 11 is coupled to the ablation handle 12 such that the outer sleeve 30 can be rotated relatively to the electrode needle body 11. Therefore, when the adjustment of the ablation needle 10 or the biopsy needle 20 is required, the position of the outer sleeve 30 can be kept unchanged, and only the ablation needle 10 or the biopsy needle 20 which is accommodated in the outer sleeve 30 can rotate, which not only reduces the friction or damage to the tissue, but also the resistance is small. In this embodiment, the distal end of the sliding member 122 defines a circular groove 1221 around a peripheral direction thereof, and the proximal end of the connecting member 121 can include a circular flange 1211 which can be engaged with the circular groove 1221. The circular flange 1211 can exactly engage with the circular groove 1221, such that the connecting member 121 can be rotatable around the axial direction of the sliding member 122, but cannot be moved in the axial direction of the sliding member 122, so that the connecting member 121 can be rotatably coupled to the sliding member 122. Moreover, during the ablation process, it is necessary to straighten out the wires and cooling pipes outside the ablation handle 12, to prevent the wires and the cooling pipes from being excessively bent and twisted, and to conveniently view the scale value on the ablation handle 12, the operator needs to rotate the ablation handle 12 and/or the ablation needle 10, specifically, the operator can hold the connector 121 by hand to keep the outer sleeve 30 from rotating, and rotate the ablation handle 12 of the ablation needle 10 to drive the electrode needle body 11 to rotate, thereby reducing the friction damage to the tissue when the outer sleeve 30 rotates, and the resistance of rotating is small.

The sliding member 122 defines a through hole extending in the axial direction of the sliding member 122. The proximal end of the electrode needle body 11 of the ablation needle 10 passes through the through hole to ensure the coaxiality of the outer sleeve 30 and the ablation needle 10. The proximal end of the electrode needle body 11 of the ablation needle 10 and the ablation handle 12 are fixedly coupled by means of bonding, snapping, pinning, or the like, which are common in this field.

The axial direction of the connecting member 121 and the axial direction of the sliding member 122 are the same as the extending direction of the electrode needle body 11 of the ablation needle 10. The adjusting member 123 can control the sliding member 122 to move along the axial direction thereof to drive the outer sleeve 30 coupled to the connecting member 121 to move relatively to the electrode needle body 11, to adjust the length of the distal end of the electrode needle body 11 protruding from the outer sleeve 30. It can be understood that, in other embodiments, the electrode needle body 11 can also be driven to move axially relatively to the outer sleeve 30 to adjust the length of the distal end of the electrode needle body 11 protruding from the outer sleeve 30. Thereby, the length of the distal end of the electrode needle body 11 protruding from the outer sleeve 30 can be adjusted according to the anatomical structure of the lesion and the actual ablation region. In this embodiment, the adjusting member 123 is located on the sliding member 122, and extends in a direction perpendicular to the extending direction of the sliding member 122. The adjusting member 123 is driven to move along a direction parallel to the axial direction of sliding member 122 so as to drive the sliding member 122 to move along the axial direction of sliding member 122. The distal end of the sliding member 122 is inserted into the proximal end of the outer sleeve 30 such that the sliding member 122 is coaxial with the outer sleeve 30. When the sliding member 122 is moved in the axial direction of sliding member 122, the outer sleeve 30 is driven to move along the axial direction of sliding member 122. In this embodiment, the distal end of the sliding member 122 is tapered, and the inner wall of the proximal end of the outer sleeve 30 is set to be tapered corresponding to the sliding member 122, so that the distal end of the sliding member 122 can be easily inserted into the outer sleeve 30 and capable of axially positioning, the assembly of the circular flange 1211 and the circular groove 1221 can be thus facilitated.

The ablation handle 12 of the ablation needle 10 can include an outer casing 124. The driving assembly 120 is accommodated in the outer casing 124. In this embodiment, the outer casing 124 can include a first casing and a second casing which are oppositely disposed, and are fixedly coupled by snapping, bonding, or the like, thereby facilitating to assemble the driving assembly 120 to the outer casing 124. The outer casing 124 defines a mounting groove 1222 along the axial direction of the sliding member 122. The mounting groove 1222 may be directly defined on the first casing or the second casing. Or, the first casing and the second casing each defines a groove, and two grooves are cooperatively fastened together to form the mounting groove 1222. The end of the adjusting member 123 away from the sliding member 122 can protrude from the mounting groove 1222. By moving the adjusting member 123 in the mounting groove 1222, the movement of the sliding member 122 in its axial direction can be thus controlled.

Figure 10:
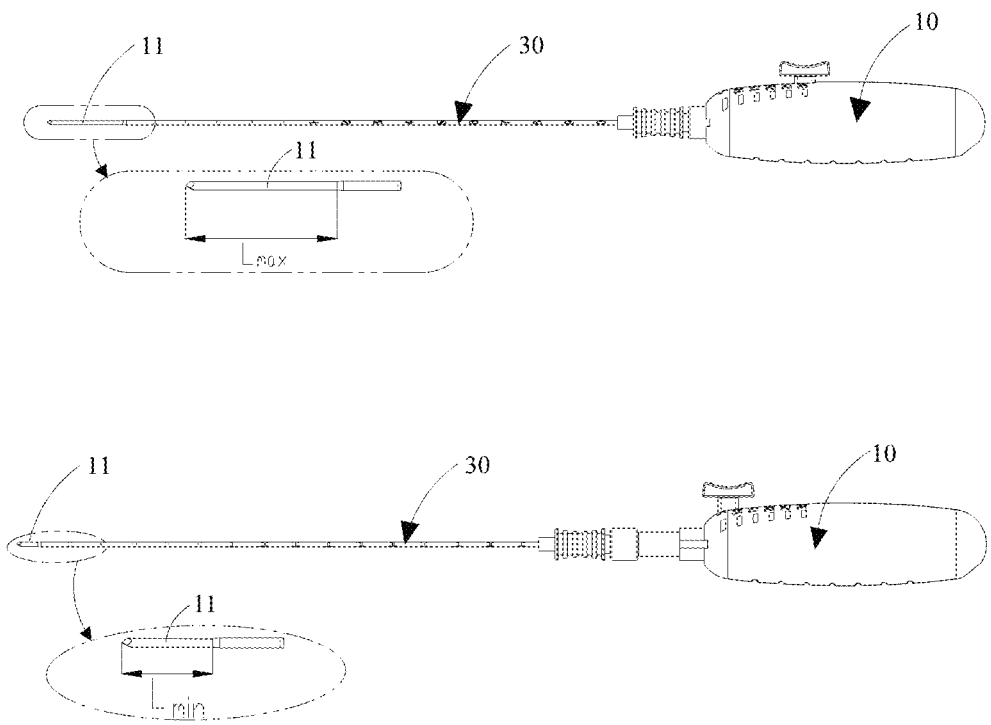
FIG. 10 is a schematic view showing a process of adjusting a length of a distal end of the ablation needle protruding from the outer sleeve after assembling the ablation needle with the outer sleeve.

Furthermore, the outer casing 124 can include a scale identification 1225 located on one side or both sides of the mounting groove 1222. After the adjusting member 123 is moved to a certain position of the mounting groove 1222, the scale value corresponding to the adjusting member 123 is observed to know the length of the ablation needle 10 protruding from the outer sleeve 30. In the case where the outer sleeve 30 is completely insulated, the length of the ablation needle 10 protruding from the outer sleeve 30 is the effective ablation length at which the ablation needle 10 can perform ablation. As shown in FIG. 10, when the outer sleeve 30 is moved to adjust the length of the ablation needle 10 protruding from the outer sleeve 30, if the adjusting member 123 is actuated to be at the nearest end of the mounting groove 1222, the scale value corresponding to the adjusting member 123 is the maximum, and the length that the ablation needle 10 protruding from the outer sleeve 30 is the longest and the length is $L_{max}$. If the adjusting member 123 is actuated to be at the farthest end of the mounting groove 1222, the scale value corresponding to the adjusting member 123 is the minimum, and the length that the ablation needle 10 protruding from the outer sleeve 30 is the shortest, and the length is $L_{min}$. It can be understood that, in other embodiments, when the ablation needle 10 is driven to move axially relatively to the outer sleeve 30, the nearest end of the mounting groove 1222 corresponds to the minimum scale value, and the farthest end of the mounting groove 1222 corresponds to the maximum scale value. It can be understood that the adjustable range of the effective ablation length of the ablation needle 10 is different according to the anatomical difference of different tissues. For example, when the ablation needle 10 is applied to the ablation treatment of hypertrophic cardiomyopathy, the adjustable range of the effective ablation length of the ablation needle 10 is about 5 mm~35 mm.

Referring to FIG. 9 to FIG. 11, the inner surface of the outer casing 124 can include a first guiding member (not shown) disposed along the axial direction of the sliding member 122, and the surface of the sliding member 122 can include a second guiding member 1223 that cooperates with the first guiding member. The sliding member 122 can slide smoothly along the axial direction thereof by the second guiding member 1223 engaged with the first guiding member. Specifically, the first guiding member may be a groove as shown in FIG. 10, and the second guiding member 1223 may be a rib located on the sliding member 122 to engage with the groove; or the first guiding member may be set to the rib and the second guiding member 1223 may be set to the groove defined on the sliding member 122 to engage with the rib.

The ablation handle 12 can further include an elastic member 125 located between the adjusting member 123 and the sliding member 122. The extending direction of the elastic member 125 faces the mounting groove 1222. The inner wall of the outer casing 124 has a plurality of latching blocks 1226 at positions corresponding to the scale identification 1225 on one side or both sides of the mounting groove 1222. The adjusting member 123 has at least one protrusion 1231. The elastic member 125 may be, but is not limited to, a spring, a spring piece, a spring washer, or the like. In the natural state, the elastic member 125 pushes the protrusion 1231 of the adjusting member 123 and is then engaged with one latching block 1226 to realize the positioning of the adjusting member 123 and the sliding member 122. The operator manually presses the adjusting member 123 downwardly, the elastic member 125 is contracted, the protrusion 1231 of the adjusting member 123 is disengaged from the latching block 1226. At this time, the sliding member 122 can be axially moved along the axial direction thereof, which causes the sliding member 122 and the outer sleeve 30 to move along the axial direction of the sliding member 122, thereby adjusting the length of the ablation needle 10 to protruding from the outer sleeve 30, that is, the effective ablation length. After the adjusting member 123 reaches a certain scale position to obtain the desired effective ablation length, the operator releases the adjusting member 123, and the elastic member 125 is elastically reset by itself, and the protrusion 1231 of the adjusting member 123 is snapped into the corresponding block 1226 so that the adjusting member 123 and the sliding member 122 can be positioned to remain stationary at the position.

Referring to FIG. 12, FIG. 13 and FIG. 16 to FIG. 18, in the present disclosure, the ablation needle assembly 100 can further include a biopsy needle 20. The ablation needle 10 and the biopsy needle 20 are alternately accommodated in the outer sleeve 30. Furthermore, the biopsy needle 20 can be detachably and rotatably coupled to the outer sleeve 30. Specifically, the biopsy needle 20 can further include a biopsy needle body 21 and a biopsy handle 22 coupled to a proximal end of the biopsy needle body 21. After the ablation needle 10 is disengaged from the outer sleeve 30, the biopsy needle body 21 of the biopsy needle 20 is inserted into the outer sleeve 30, and the outer sleeve 30 is detachably and rotationally coupled to the biopsy handle 22 of the biopsy needle 20. In other words, the ablation needle 10 can be detachably coupled to the outer sleeve 30, and the biopsy needle 20 can also be detachably coupled to the outer sleeve 30. After the ablation needle 10 and the outer sleeve 30 are disengaged, the biopsy needle 20 can be coupled to the outer sleeve 30. Therefore, after the ablation operation is completed, the connection of the ablation needle 10 to the outer sleeve 30 is released, and the outer sleeve 30 is left in the tissue to provide a channel for the biopsy operation, so that the biopsy needle 20 quickly reaches a desired biopsy position to obtain the tissue to be biopsied, thereby avoiding repeated puncture to reduce tissue damage. Alternatively, during some surgical procedures, after the biopsy operation is completed, the biopsy needle 20 and the outer sleeve 30 are disengaged, the outer sleeve 30 is left in the tissue to provide a channel for the ablation operation, so that the ablation needle 10 can quickly reach a desired ablation position. Moreover, the outer sleeve 30 is detachably and rotationally coupled with the biopsy needle body 21, so that during the biopsy operation, if the biopsy needle 20 needs to be rotated, the outer sleeve 30 can be kept stationary, thereby reducing tissue damage, and the resistance of rotating is small. Thus, the surgical effect can be evaluated by the biopsy needle 20 performing biopsy before and/or after ablation, and the biopsy tissue can be a body fluid, a muscle, or the like. When the biopsy tissue is a body fluid, a vacuum generating device can also be inserted into the proximal end of the biopsy needle 20 to draw out the body fluid.

Referring to FIG. 14, FIG. 15 and FIG. 19 to FIG. 23, furthermore, in some embodiments of the present disclosure, the ablation needle assembly 100 can further include a puncture needle 40. The diameter of the puncture needle 40 is slightly larger than the diameter of the ablation needle 10 or the biopsy needle 20, and the diameter of the puncture needle 40 preferably ranges from 19G to 16G. And the puncture needle 40 is preferably made of hard materials such as stainless steel. The puncture needle 40, the ablation needle 10 or the biopsy needle 20 is alternately accommodated in the outer sleeve 30 and detachably coupled to the outer sleeve 30. The distal end of the puncture needle 40 protrudes from the outer sleeve 30. In this embodiment, the distal end of the puncture needle 40 has a sharp needle shape or a triangular pyramid shape, and its proximal end can fix a joint 41 having an internal thread. The internal thread of the joint 41 is engaged with the external thread of the proximal end of the outer sleeve 30. After adding the puncture needle 40, the puncture needle 40 and the outer sleeve 30 can be assembled to puncture before the ablation or the biopsy, then the connection between the puncture needle 40 and the outer sleeve 30 is released, the puncture needle 40 is withdrawn, and the ablation needle 10 or biopsy needle 20 is inserted into the outer sleeve 30. The larger diameter and harder puncture needle 40 can provide better support for the outer sleeve 30, so the combination of the puncture needle 40 and the outer sleeve 30 is more convenient for puncturing, and can prevent the ablation needle 10 or the biopsy needle 20 from being damaged when directly using the ablation needle 10 or the biopsy needle 20 to puncture.

Figure 6:
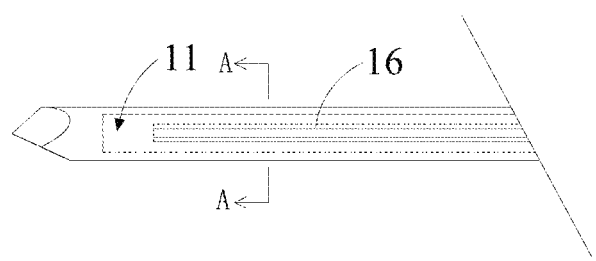
FIG. 6 is an enlarged view of distal end of electrode needle body according to one embodiment of the present disclosure.
Figure 7:
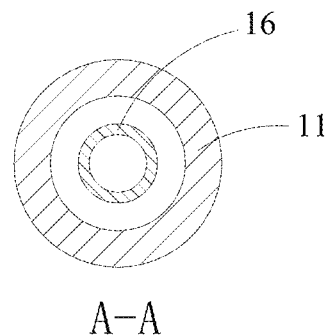
FIG. 7 is a cross-sectional view of electrode needle body shown in FIG. 6 taken along a line A-A.

Furthermore, please referring to FIG. 2, FIG. 6, and FIG. 24 together, the present disclosure further provides an ablation system 200, including the ablation needle assembly 100 and the energy generating device 210. In some embodiments of the present disclosure, the ablation system 200 can further include a medical imaging device 220 and/or a cold source supply device 230. The energy generating device 210 is electrically coupled to the ablation needle 10, and the energy generating device 210 can be, but is not limited to, a radio-frequency generator or a microwave generator. The cold source supply device 230 interconnects with the cooling channel 16 through a cooling conduit 260 to provide a gaseous or liquid cooling medium to the cooling channel 16 to cool the high temperature portion sensed by the temperature sensor 50 in order to control the temperature when ablating.

The medical imaging device 220 is configured to display the distal position of the outer sleeve 30 and the ablation needle 10 in real-time, and may be selected from at least one of ultrasonography, CT, MRI, and fluoroscopy, preferably ultrasonography. The medical imaging device 220 is configured to monitor the ablation position during the operation and also display the relative position of the needle body at the ablation position. The medical imaging device 220 itself can collect, process the data and display the image. The corresponding sensing components in or out of the patient body collecting positional state parameters can also be coupled to the medical imaging device 220, and the information collected by the sensing components is added when the image is displayed, which is more surgically meaningful.

Preferably, the ablation system 200 can further include a simulated navigation device 240 indicating the ablation position and the relative position of the ablation needle 10 at the ablation position. The simulated navigation device 240 may be one or more of magnetic navigation, infrared navigation, and optical navigation.

Preferably, the simulated navigation device 240 performs three-dimensional modeling of the heart according to the information collected by the medical imaging device 220 to obtain a cardiac model at least including a ventricular septum model. Specifically, the simulated navigation device 240 can collect basic data of the patient's heart, including four data [TropI, myoglobin (Mb), creatine kinase isoenzyme mass (CK-MBmass), B-type forebrain natriuretic peptide] of myocardial injury, heart rhythm, routine electrocardiogram and 24-hours dynamic electrocardiogram, echocardiogram, ventricular wall thickness, location and extent of myocardial fibers, coronary angiography, and the like, so as to perform three-dimensional modeling of the heart. The hypertrophic ventricular septum portion can be measured and displayed by the simulated navigation device 240, and is marked on the cardiac model as the area to be ablated, and in the use state, the simulated navigation device 240 collects the position of the ablation needle assembly 100 in real-time by the medical imaging device 220 and displays it at the corresponding position of the cardiac model as a real-time monitoring and guidance of the operation.

Furthermore, the simulated navigation device 240 may display information such as a conduction beam, a position of cardiac apex, and a coronary vessel distribution in the cardiac model. On one hand, the simulated navigation device 240 indicates the ablation position to be ablated, the ablation time to be ablated, and the corresponding ablation energy, on the other hand, the simulated navigation device 240 also plans an advancement path of the ablation needle 10 according to the cardiac model. Specifically, the simulated navigation device 240 can comprehensively analyze the ex vivo experiment, animal experiment and clinical record data before surgery, calculate the thermophysical parameters of the ventricular septum myocardium with temperature from the bio-heat equation, calculate the correspondence relationship between the ablation region to be ablated, the ablation time and the ablation energy, and the like, and plan the advancement path of the ablation needle 10.

Specifically, the advancement path of the ablation needle 10 is generally the ablation needle 10 punctures through the intercostal, the epicardium of the cardiac apex, the cardiac apex in sequence, and then punctures into the ventricular septum. The ablation needle 10 should advance along the middle of the ventricular septum without damaging the endocardium on two sides of the ventricular septum, avoiding influence and contact the conductive bundle located under the endocardium on two sides of the ventricular septum. It is worth noting that the advancement path of the ablation needle 10 preferably avoids the arteries and veins of the intercostal, and coronary arteries and veins of the cardiac apex; for patients with apical ventricular aneurysm, it is necessary to avoid damage to the ventricular aneurysm.

Furthermore, the simulated navigation device 240 collects the electrocardiogram signal in real-time, and prompts an alarm when the electrocardiogram signal meets an abnormality determination condition. Specifically, the electrocardiogram function of the human body can be monitored during the operation, and when the electrocardiogram changes such as premature beats occur, it can be regarded as a warning signal, and the position of the ablation needle 10 is marked at this time.

Furthermore, the simulated navigation device 240 collects the position of the ablation needle 10 in real-time and compares it with a planned ablating path, and presents an alarm when the deviation reaches an abnormal determination condition.

For example, the simulated navigation device 240 determines the position of the conductive beam by recording a change of the electrocardiogram during a puncturing process using the ablation needle 10, and gives the operator a warning message. The simulated navigation device 240 can also predict the next action of the ablation needle 10 according to the ablating path and the ablation power, and can re-plan the ablating path according to the real-time situation of the operation to guide the operator and further improve the operation success rate.

Furthermore, the ablation system 200 can further include a guiding device 250 for holding and changing the spatial position of the ablation needle 10. The guiding device 250 can include a three-dimensional adjusting frame and a support mounted on the three-dimensional adjusting frame. The ablation needle 10 is fixed on the support. The guiding device 250 can cooperate with the ultrasonography to guide the ablation needle 10 to puncture. The guiding device 250 may be in a form of a three-dimensionally moving robotic arm or the like, and may also provide multi-axis rotation. Furthermore, the ablation needle 10 is one or more, and each ablation needle 10 is independently driven by the guiding device 250.

Furthermore, the ablation system 200 can further include a retrievable vascular filter (not shown) for placing in the ascending aorta prior to ablation or during ablation to prevent complications of embolism. In order to prevent thrombosis, embolus, or other tissue shedding during ablation therapy or a period after ablation, especially in the process of ablating the ventricular septum myocardium, left ventricular thrombus, embolism or other tissue loss with blood flow into the aorta, a complication of cerebral embolism or other tissue embolism may occur, a retrievable vascular filter is placed in the ascending aorta, filtering thrombus, embolus or other tissue shedding in the form of a sieve without obstructing blood flow in the aorta to achieve prevention of complications of embolism. Furthermore, the retrievable vascular filter can include a main filter mesh, a filter connecting member, and a guide wire for placing vascular filter. Furthermore, the main filter mesh is woven from medical nickel-titanium wire, the material of the filter connecting member is ultra-smooth coated stainless steel, and the material of the guide wire is ultra-smooth coated stainless steel, 4-5 mm in diameter.

At the time of surgery, the ablation needle assembly 100 performs ablation to the posterior ventricular septum after it reaches the predetermined ablation position according to the predetermined advancement path, then the ablation needle assembly 100 performs ablation to the anterior ventricular septum, so that the ablation region completely covers the hypertrophic position in the thickness direction of the ventricular septum. The ablation needle 10 is then withdrawn a certain distance and the energy generating device 210 is activated for ablating, thereby performing treatment for a plurality of different hypertrophic locations. Of course, depending on the specific location and thickness of the hypertrophy, the anterior ventricular septum or the middle ventricular septum can also be reached initially or approached. In order to reduce myocardial trauma, the ablation needle 10 preferably remains unextracted from epicardium of the cardiac apex during inserting of the ablation needle 10 into the ventricular septum and reaching different hypertrophic positions of the ventricular septum.

Furthermore, the ablation system 200 can further include a data processing device 270. Preferably, a temperature sensor 50 is provided in the cavity of the distal end of the electrode needle body 11. The temperature sensor 50 is electrically coupled to the data processing device 270. The temperature sensor 50 performs temperature monitoring during ablation. The data processing device 270 adjusts the output parameters of the energy generating device 210 according to the result of the temperature monitoring. The data processing device 270 controls to issue an alarm when it is determined that the temperature monitoring value exceeds the set upper temperature limit.

Compared with the prior art, the present disclosure utilizes the ablation needle 10 to puncture the ventricular septum from the intercostal and the cardiac apex in sequence, and then releases energy to ablate the hypertrophic ventricular septum myocardium to treat hypertrophic cardiomyopathy, thereby avoiding the risk and pain of surgical septal myectomy and extracorporeal circulation in surgical resection, and there is no risk of large-area myocardial infarction caused by alcohol ablation of target vessels or alcohol spillover. It is easy to operate, the patient's trauma is extremely slight, the operation risk is low, and the curative effect is remarkable.

Please refer to FIG. 16 to FIG. 18 and FIG. 25 to illustrate the flowchart of the treatment method for hypertrophic cardiomyopathy according to one embodiment of the present disclosure.

In step S2501, the ablation needle 10 is movably accommodated in the outer sleeve 30 firstly, and the outer sleeve 30 is coupled to the ablation handle 12 of the ablation needle 10 through the connecting member 121 to obtain the ablation needle assembly 100 as shown in FIG. 2.

In step S2502, the distal end of the ablation needle assembly 100 is advanced from an outside of a body through an intercostal and a cardiac apex into a ventricular septum.

Step S2503, the energy generating device 210 is turned on, and the hypertrophied myocardium within the ventricular septum is subjected to radio-frequency ablating or microwave ablating using the distal end of the ablation needle assembly 100 to destroy the activity of the hypertrophied myocardium within the ventricular septum, so that the hypertrophied myocardium within the ventricular septum becomes necrotic and/or atrophic.

Specifically, in one embodiment, the portion of the ablation needle 10 protruding from the outer sleeve 30 performs radio-frequency ablating or microwave ablating to the hypertrophied myocardium within the ventricular septum.

Furthermore, the treatment method for hypertrophic cardiomyopathy can further includes the step of: when the assembly of the outer sleeve 30 and the ablation needle 10 is advanced from the outside of the body through the intercostal and the cardiac apex into the ventricular septum, the scale value of the outer sleeve 30 corresponding to the patient's body surface is known as the depth of the outer sleeve 30 advancing into the body.

Furthermore, the treatment method for hypertrophic cardiomyopathy further includes the step of: before or during ablation process, adjusting the length of the distal end of the electrode needle body 11 protruding from the outer sleeve 30.

Specifically, the outer sleeve 30 is driven by the driving assembly 120 to move relatively to the electrode needle body 11 along the extending direction of the electrode needle body 11 to adjust the length of the distal end of the electrode needle body 11 protruding from the outer sleeve 30.

Furthermore, the adjusting member 123 is manually pressed downwardly, so that the adjusting member 123 presses the elastic member 125 and the lower end of the adjusting member 123 is separated from the latching block 1226; the adjusting member 123 drives the sliding member 122 and the outer sleeve 30 to move in the axial direction of the sliding member 122 to adjust the length of the distal end of the electrode needle body 11 protruding from the outer sleeve 30; when the adjusting member 123 reaches a certain scale position to obtain a desired effective ablation length, the adjusting member 123 is loosened, and the elastic member 125 elastically resets and pushes the lower end of the adjusting member 123 into the corresponding latching block, so that the adjusting member 123 and the sliding member 122 can be positioned and remain stationary.

Furthermore, the treatment method for hypertrophic cardiomyopathy can further include the step of: determining the length of the distal end of the electrode needle body 11 protruding from the outer sleeve 30 according to the scale identification on the ablation handle 12 while adjusting the length of the distal end of the electrode needle body 11 protruding from the outer sleeve 30.

Furthermore, the treatment method for hypertrophic cardiomyopathy can further include the step of: adjusting an ablation region and an ablation orientation of the ablation needle 10 by rotating the outer sleeve 30 relatively to the ablation needle 10 or rotating the outer sleeve 30 relatively to the ablation needle 10 to expose different regions of the ablation needle 10.

Furthermore, when the outer sleeve 30 is rotated relatively to the ablation needle 10, the operator holds the connecting member 121 to keep the outer sleeve 30 from rotating, and rotates the ablation handle 12 to drive the ablation needle 10 to rotate relatively to the outer sleeve 30.

Furthermore, the treatment method for hypertrophic cardiomyopathy can further include the steps of: the temperature sensor 50 performs temperature monitoring during the ablation process; and the data processing device 270 adjusts the output parameter of the energy generating device 210 according to the result of the temperature monitoring: Furthermore, the data processing device 270 controls to issue an alarm when it is determined that the temperature monitoring value exceeds the set upper temperature limit.

Furthermore, the treatment method for hypertrophic cardiomyopathy can further include the step of: delivering the cooling medium through the cooling channel 16 to cool the high temperature portion sensed by the temperature sensor 50 to control the temperature during the ablation process.

Furthermore, the treatment method for hypertrophic cardiomyopathy can further include the step of: advancing the distal end of the ablation needle assembly from the outside of the body through the intercostal and the cardiac apex into the ventricular septum along a predetermined advancement path, wherein the advancement path is:

through the intercostal and an epicardium of the cardiac apex, then along a middle of the ventricular septum without damaging the endocardium on two sides of the ventricular septum, avoiding arteries and veins of the intercostal, and coronary arteries and veins of the cardiac apex; for patients with apical ventricular aneurysm, avoiding damage to the ventricular aneurysm.

Furthermore, the ablation system 200 further comprises a medical imaging device 220, and the distal end of the outer sleeve 30 has a first guiding portion 34 that is detected by the medical imaging device 220, the treatment method for hypertrophic cardiomyopathy can further include the steps of: determining whether the outer sleeve 30 is advanced along a predetermined advancement path according to a visualisation of the first guiding portion 34 under the medical imaging device 220 during the puncturing process, and whether it is close to a predetermined ablation position;

Furthermore, the distal end of the electrode needle body 11 has a second guiding portion 17 capable of being detected by the medical imaging device 220, the treatment method for hypertrophic cardiomyopathy can further include the step of: determining whether the distal end of the electrode needle body 11 advances along a predetermined advancement path and whether it reaches a predetermined ablation position according to a visualisation of the second guiding portion 17 under the medical imaging device 220.

Figure 17:
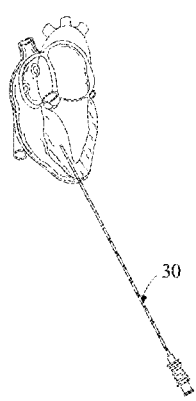
Figure 18:
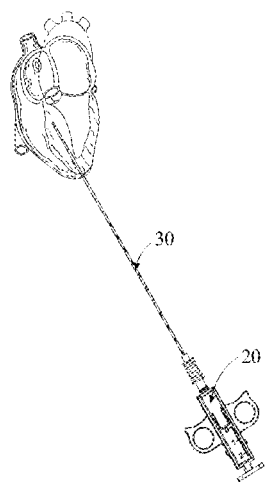
Figure 23:
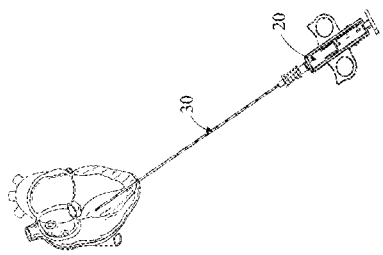
FIG. 19 to FIG. 23 are schematic diagrams showing a use process of the ablation needle assembly according to another embodiment of the present disclosure.
Figure 22:
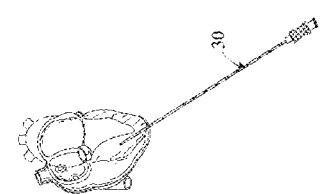
Figure 21:
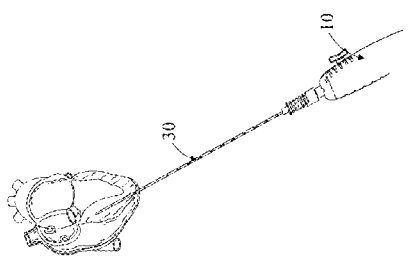
Figure 20:
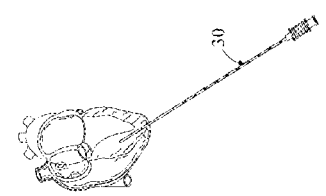
Figure 19:
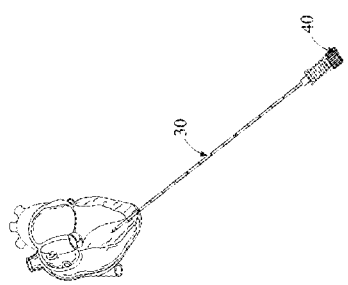

As shown in FIG. 17 and FIG. 18, in the case where the ablation operation is required and the biopsy operation is also required, the treatment method for hypertrophic cardiomyopathy can further include the steps of: after the ablation is performed, releasing the outer sleeve 30 from the connecting member 121; withdrawing the ablation needle 10 and leaving the outer sleeve 30, and then inserting the biopsy needle 20 into the outer sleeve 30 to extract a tissue sample for biopsy.

The outer sleeve 30 provides a channel to the biopsy procedure, avoids repeated punctures, reduces tissue damage, and enables the biopsy needle 20 to reach the desired biopsy position quickly.

It can be understood that, in some cases, the outer sleeve 30 and the biopsy needle 20 may be assembled for puncture and biopsy before the ablation is performed, and then the biopsy needle 20 is withdrawn to leave the outer sleeve 30, and then the adjusting member 123 is actuated to enable the driving assembly 120 to arrive at a desired scale position, finally the ablation needle 10 is inserted into the outer sleeve 30, and establish the connection of the outer sleeve 30 and the connecting member 121 by rotating the connecting member 121, and the ablation needle 10 performs ablation with the desired effective ablation length, which avoids repeated puncture and reduces tissue damage.

As shown in FIG. 19 to FIG. 23, in some embodiments of the present disclosure, after the ablation needle assembly 100 is added with a puncture needle 40, the treatment method for hypertrophic cardiomyopathy can further include the steps of: before ablation or biopsy, assembling the puncture needle 40 and the outer sleeve 30 to puncture so as to increase the puncture strength; releasing the connection between the puncture needle 40 and the outer sleeve 30; withdrawing the puncture needle 40, leaving the outer sleeve 30 in the ventricular septum; and inserting the ablation needle 10 or the biopsy needle 20 into the outer sleeve 30 to perform ablation or biopsy operation, so as to prevent the ablation needle 10 or biopsy needle 20 from being damaged during the puncture process.

The above is a preferred embodiment of the present disclosure, and it should be noted that those skilled in the art may make some improvements and modifications without departing from the principle of the present disclosure, and these improvements and modifications are also in the protection scope of the present disclosure.

What is claimed is:

1. A treatment method for hypertrophic cardiomyopathy, applied to an ablation system, the ablation system comprising an ablation needle assembly and an energy generating device coupled to the ablation needle assembly, the treatment method for hypertrophic cardiomyopathy comprising:

advancing a distal end of the ablation needle assembly from an outside of a body through an intercostal and a cardiac apex into a ventricular septum;

turning on the energy generating device, and using the distal end of the ablation needle assembly to perform radio-frequency ablation or microwave ablation to hypertrophied myocardium within the ventricular septum, destroying activity of the hypertrophied myocardium within the ventricular septum, and making the hypertrophied myocardium within the ventricular septum necrotic and/or atrophic.

2. The treatment method for hypertrophic cardiomyopathy according to claim 1, wherein the ablation needle assembly comprises a hollow outer sleeve and an ablation needle that is movably accommodated in the outer sleeve; the using the distal end of the ablation needle assembly to perform radio-frequency ablation or microwave ablation to hypertrophied myocardium within the ventricular septum comprises:

performing radio-frequency ablation or microwave ablation to the hypertrophied myocardium within the ventricular septum using a portion of the ablation needle protruding from the outer sleeve.

3. The treatment method for hypertrophic cardiomyopathy according to claim 2, wherein an outer surface of the outer sleeve comprises a scale identification, and the treatment method for hypertrophic cardiomyopathy further comprises:

determining a depth of the outer sleeve advancing into the body according to the scale identification corresponding to body surface when an assembly of the outer sleeve and the ablation needle is advanced into the ventricular septum from the outside of the body through the intercostal and the cardiac apex.

4. The treatment method for hypertrophic cardiomyopathy according to claim 2, wherein the ablation needle comprises an electrode needle body and an ablation handle coupled to a proximal end of the electrode needle body, the outer sleeve is sleeved on the electrode needle body and is detachably coupled to the ablation handle, before or after advancing a distal end of the ablation needle assembly from an outside of a body through an intercostal and a cardiac apex into a ventricular septum, the treatment method for hypertrophic cardiomyopathy further comprises:

adjusting a length of a distal end of the electrode needle body protruding from the outer sleeve.

5. The treatment method for hypertrophic cardiomyopathy according to claim 4, wherein the ablation handle comprises a driving assembly coupled to the outer sleeve, the adjusting a length of a distal end of the electrode needle body protruding from the outer sleeve comprises:
   driving the outer sleeve to move relatively to the electrode needle body along an extending direction of the electrode needle body by the driving assembly to adjust the length of the distal end of the electrode needle body protruding from the outer sleeve.

6. The treatment method for hypertrophic cardiomyopathy according to claim 5, wherein the outer sleeve and the ablation needle are relatively rotatable; an outer surface of the outer sleeve is entirely coated with an insulating layer, and a distal end of the outer sleeve defines one or several hollow region disposed axially or circumferentially, and the treatment method for hypertrophic cardiomyopathy further comprises:
   causing the outer sleeve to rotate relatively to the ablation needle or causing the outer sleeve to move relatively to the ablation needle to expose different regions of the ablation needle to adjust an ablation region and an ablation orientation of the ablation needle.

7. The treatment method for hypertrophic cardiomyopathy according to claim 6, wherein the ablation handle further comprises a connecting member rotatably coupled to the driving assembly, the outer sleeve being detachably coupled to the connecting member; the causing the outer sleeve to rotate relatively to the ablation needle comprises: the operator holding the connecting member to keep the outer sleeve from rotating, and causing the ablation needle to rotate relatively to the outer sleeve by rotating the ablation handle.

8. The treatment method for hypertrophic cardiomyopathy according to claim 7, wherein the ablation handle further comprises an outer casing accommodating the driving assembly, the driving assembly comprises a sliding member axially disposed and an adjusting member coupled to the sliding member, and the ablation handle further comprises an elastic member located between the adjusting member and the sliding member, the outer casing defines a mounting groove disposed along an axial direction of the sliding member, and further comprises a plurality of latching blocks disposed under the mounting groove, the elastic member pushes a lower end of the adjusting member into the latching block to realize positioning of the adjusting member and the sliding member; the treatment method for hypertrophic cardiomyopathy further comprises:
   pressing the adjusting member downwardly, causing the adjusting member to press the elastic member and separating the lower end of the adjusting member from the latching block;
   pushing the adjusting member axially to move the sliding member and the outer sleeve to move axially to adjust the length of the distal end of the electrode needle body protruding from the outer sleeve;
   after obtaining a desired length, loosing the adjusting member, and the elastic member elastically resetting to push the lower end of the adjusting member into the corresponding latching block so that the adjusting member and the sliding member are positioned at a position of the corresponding latching block.

9. The treatment method for hypertrophic cardiomyopathy according to claim 8, wherein the outer casing comprises a scale identification, and the treatment method for hypertrophic cardiomyopathy further comprises:
   the length of the distal end of the electrode needle body protruding from the outer sleeve is determined according to the scale identification in a course of adjusting the length of the distal end of the electrode needle body protruding from the outer sleeve.

10. The treatment method for hypertrophic cardiomyopathy according to claim 9, wherein the electrode needle body defines a cooling channel, the treatment method for hypertrophic cardiomyopathy further comprises:
    delivering cooling medium through the cooling channel to cool a high temperature portion to control temperature during ablation process.

11. The treatment method for hypertrophic cardiomyopathy according to claim 4, wherein the advancing a distal end of the ablation needle assembly from an outside of a body through an intercostal and a cardiac apex into a ventricular septum, comprises:
    advancing the distal end of the ablation needle assembly from the outside of the body through the intercostal and the cardiac apex into the ventricular septum along a predetermined advancement path, wherein the advancement path is:
    through the intercostal and the cardiac apex, then along a middle of the ventricular septum without damaging the endocardium on two sides of the ventricular septum, avoiding arteries and veins of the intercostal, and coronary arteries and veins of the cardiac apex; for patients with apical ventricular aneurysm, avoiding damage to the ventricular aneurysm.

12. The treatment method for hypertrophic cardiomyopathy according to claim 11, wherein the ablation system further comprises a medical imaging device, and the distal end of the outer sleeve has a first guiding portion capable of being detected by the medical imaging device, the treatment method for hypertrophic cardiomyopathy further comprises:
    during a puncturing process, determining whether the outer sleeve is advanced along a predetermined advancement path and whether it is close to a predetermined ablation position according to a visualization of the first guiding portion under the medical imaging device.

13. The treatment method for hypertrophic cardiomyopathy according to claim 12, wherein the distal end of the electrode needle body has a second guiding portion capable of being detected by the medical imaging device, and the treatment method for hypertrophic cardiomyopathy further comprises:
    during the puncturing process, determining whether the distal end of the electrode needle body is advanced along a predetermined advancement path and whether it reaches a predetermined ablation position according to a visualization of the second guiding portion under the medical imaging device.

14. The treatment method for hypertrophic cardiomyopathy according to claim 13, wherein the medical imaging device is an ultrasonograph.

15. The treatment method for hypertrophic cardiomyopathy according to claim 13, wherein the treatment method for hypertrophic cardiomyopathy further comprises:
    performing ablation to a posterior ventricular septum after the ablation needle and the outer sleeve reach a predetermined ablation position according to the predetermined advancement path, then performing ablation to an anterior ventricular septum, so that ablation region completely covers hypertrophic position in a thickness direction of the ventricular septum; and withdrawing the ablation needle at a distance to treat different hypertrophic position within the ventricular septum.

16. The treatment method for hypertrophic cardiomyopathy according to claim 15, wherein the treatment method for hypertrophic cardiomyopathy further comprises:
during inserting the ablation needle into the ventricular septum and reaching different hypertrophic positions of the ventricular septum, the ablation needle remains in the epicardium of the cardiac apex.

17. The treatment method for hypertrophic cardiomyopathy according to claim 2, wherein the ablation needle assembly further comprises a biopsy needle, the ablation needle and the biopsy needle are alternately accommodated in the outer sleeve, the treatment method for hypertrophic cardiomyopathy further comprises:
detachably mounting the biopsy needle in the outer sleeve before and/or after ablating of the hypertrophied myocardium within the ventricular septum; and
extracting biopsy tissue through the biopsy needle.

18. The treatment method for hypertrophic cardiomyopathy according to claim 17, wherein the ablation needle assembly further comprises a puncture needle, the puncture needle, the ablation needle or the biopsy needle is alternately accommodated in the outer sleeve and detachably coupled to the outer sleeve, the treatment method for hypertrophic cardiomyopathy further comprises:
before the ablation or before the biopsy, advancing an assembly of the puncture needle and the outer sleeve from the outside of the body through the intercostal and the cardiac apex into the ventricular septum;
leaving the outer sleeve in the ventricular septum, and withdrawing the puncture needle from the outer sleeve in order to replace with the ablation needle for ablation or replace with the biopsy needle for biopsy.

19. The treatment method for hypertrophic cardiomyopathy according to claim 1, wherein the ablation system further comprises a retrievable vascular filter, the treatment method for hypertrophic cardiomyopathy further comprising:
placing the retrievable vascular filter in ascending aorta prior to or during ablation.

* * * * *